(12) United States Patent
Elliott

(10) Patent No.: US 7,604,998 B2
(45) Date of Patent: Oct. 20, 2009

(54) FINGERPRINT ANALYSIS FOR A PLURALITY OF OLIGONUCLEOTIDES

(75) Inventor: Brian Elliott, Coralville, IA (US)

(73) Assignee: Integrated DNA Technologies, Inc, Skokie, IL (US)

(*) Notice: Subject to any disclaimer, the term of this patent is extended or adjusted under 35 U.S.C. 154(b) by 20 days.

(21) Appl. No.: 11/876,960

(22) Filed: Oct. 23, 2007

(65) Prior Publication Data

US 2008/0102531 A1    May 1, 2008

Related U.S. Application Data

(60) Provisional application No. 60/863,063, filed on Oct. 26, 2006.

(51) Int. Cl.
*G01N 33/00*    (2006.01)
*G01N 24/00*    (2006.01)
*C12Q 1/68*    (2006.01)

(52) U.S. Cl. .................. 436/94; 436/171; 436/173; 435/6; 702/19

(58) Field of Classification Search .............. 436/63, 436/94, 164, 171, 173; 435/6; 536/23.1; 702/19, 20
See application file for complete search history.

(56) References Cited

U.S. PATENT DOCUMENTS

| 6,281,493 | B1* | 8/2001 | Vestal et al. ............... 250/287 |
| 6,558,902 | B1* | 5/2003 | Hillenkamp ................ 506/6 |
| 6,613,509 | B1* | 9/2003 | Chen .......................... 435/6 |
| 2004/0079878 | A1* | 4/2004 | Vestal et al. ............... 250/287 |
| 2004/0126772 | A1* | 7/2004 | Hayashizaki et al. ........ 435/6 |

OTHER PUBLICATIONS

Elliott, Brian. Integrated DNA Technologies, 2005, pp. 1-8.*
Hail et al. American Biotechnology Laboratory, Jan. 2004, pp. 12-14.*

* cited by examiner

*Primary Examiner*—Maureen M Wallenhorst

(57) ABSTRACT

The invention provides a method for evaluating the accuracy of an oligonucleotide sample, specifically a sample containing a variety of oligonucleotides of potentially varying size and sequence. The method provides a fingerprint that can be used to evaluate the accuracy of a multi-oligonucleotide sample whether or not the sample contains differing oligonucleotides that have the same or about the same molecular weight.

11 Claims, 8 Drawing Sheets

FINGERPRINT ANALYSIS FOR A PLURALITY OF OLIGONUCLEOTIDES

CROSS-REFERENCE TO RELATED APPLICATION

The present application claims priority under 35 U.S.C. § 119(e) to U.S. provisional patent application No. 60/863,063 filed 26 Oct. 2006. The entire teachings of the above application are incorporated herein by reference.

FIELD OF THE INVENTION

This invention pertains to the post-synthetic analysis and validation of oligonucleotides, specifically the post-synthetic analysis and validation of a plurality of oligonucleotides.

BACKGROUND OF THE INVENTION

Oligonucleotides are used in a multitude of research and clinical applications. Ensuring the integrity of the oligonucleotide is vital to prevent failures or misleading results in applications using the oligonucleotides. Several methods have been developed to ensure that the resulting oligonucleotide is what the technician intended for use in their application.

One method of ensuring quality during the synthesis of the oligonucleotide is through trityl monitoring. The dimethoxytrityl (DMT) group that is used for capping the 5'-hydroxyl group of the monomers in the oligonucleotide synthesis fluoresces in its protonated form after it is removed with an acid. The absorbance of the fluorescence can be measured at or around 498 nm. A decrease in the absorbance level can be an indication that coupling was inefficient.

The identity of an oligonucleotide target can be assessed post-synthetically by measuring the predominant molecular weight of the population. The target sequence is known, so the calculated molecular weight of the bases themselves is the standard by which one compares the measured molecular weight to see if the desired compound was created. One way of utilizing this principle is through matrix assisted laser desorption ionization time-of-flight mass spectrometry (MALDI-TOF). MALDI-TOF uses laser light in conjunction with a chemical matrix to impart a charge to the sample in question and repel it from the sample plate. The resulting ions travel through a flight tube to the detector, which measures particle counts as a function of time. The time-of-flight (TOF) is directly proportional to the mass of the molecule.

MALDI-TOF is a robust and incredibly high-throughput process for assessing molecular weight. One drawback of MALDI-TOF is that the ionization efficiency (and therefore the resolution) of the procedure drops rapidly above ~45 bases or >13,000 Da. With the popularity of 70 mer arrays and long oligonucleotides for cloning and/or gene synthesis, another method is needed to assess longer products.

Electrospray ionization (ESI) mass spectroscopy ionizes target molecules such as oligonucleotides into multiple charge states. The readout of these charge states is a waveform that can be deconvoluted into parent peaks. The method uses a tight m/z window of 500-1,500, which gives it high mass accuracy. As only the charge state will vary for the ions, oligonucleotides with high molecular weights can be analyzed using this method. Therefore ESI is often a preferred quality control (QC) method over MALDI-TOF for longer oligonucleotides (see Elliott, B. and Hail, M. High-Throughput Analysis of Oligonucleotides Using Automated Electrospray Ionization Mass Spectrometry American Biotechnology Laboratory, January 2004).

Currently the use of ESI and MALDI-TOF in quality control is limited to comparing the results of the ESI to the expected peak that would result from an oligonucleotide sequence of that given molecular weight. Some assays can use 48, 96 or greater oligonucleotide sequences for the given assay, and a given sequence may be indistinguishable from other sequences in the assay based upon molecular weight alone. The quality control of an assay is therefore reliant on running the assay through the given platform to ensure that the results of the assay equate to the expected results.

Other methods are known in the art that observed multi-oligonucleotide samples to detect the presence or absence of a single nucleotide polymorphism (see Koster et al., U.S. Pat. No. 7,074,563), but this assay can not detect the presence or absence of any constituent oligonucleotide in an oligonucleotide mixture and its relative concentration therein.

The proposed method involves generating a theoretical MALDI-TOF or ESI trace (fingerprint) of a multi-oligonucleotide sample and then comparing the actual MALDI-TOF or ESI data of the mix to the fingerprint as a QC check.

BRIEF SUMMARY OF THE INVENTION

The proposed method involves generating a theoretical ESI trace (fingerprint) and then comparing the actual ESI trace data of the mix to the fingerprint to verify the accuracy of the syntheses. The method enables multiple data points from the ESI data to be graphically represented even if more than one oligonucleotide sequence in the assay shares the same data point. The theoretical trace assigns a signal value of one to each discrete mass, i.e. a molecular weight range that has no overlap with another range would be assigned a value of one. If more than one mass appears at a respective molecular weight, the intensity is increased by that number (e.g. if three different oligonucleotides in the assay would have the same molecular weight, then the range would be assigned an intensity value of 3). The number of peaks would be further pared back by assuming that any that crossed at 50% or more of the peak height would be additive. The width of the peak is dependent on the length of the sample oligonucleotide. The new peak's mass would be calculated using the following formula:

$$MW_{new} = (MW_1 * Intensity_1 + MW_2 * Intensity_2 + \ldots MW_n * Intensity_n)/(Intensity_1 + Intensity_2 + \ldots Intensity_n)$$

The new peak intensity is simply the addition of the individual intensities.

The inventive method is not limited to any particular assay format, and it could also be used to fingerprint MALDI-TOF results.

DETAILED DESCRIPTION OF THE INVENTION

Figure 1:
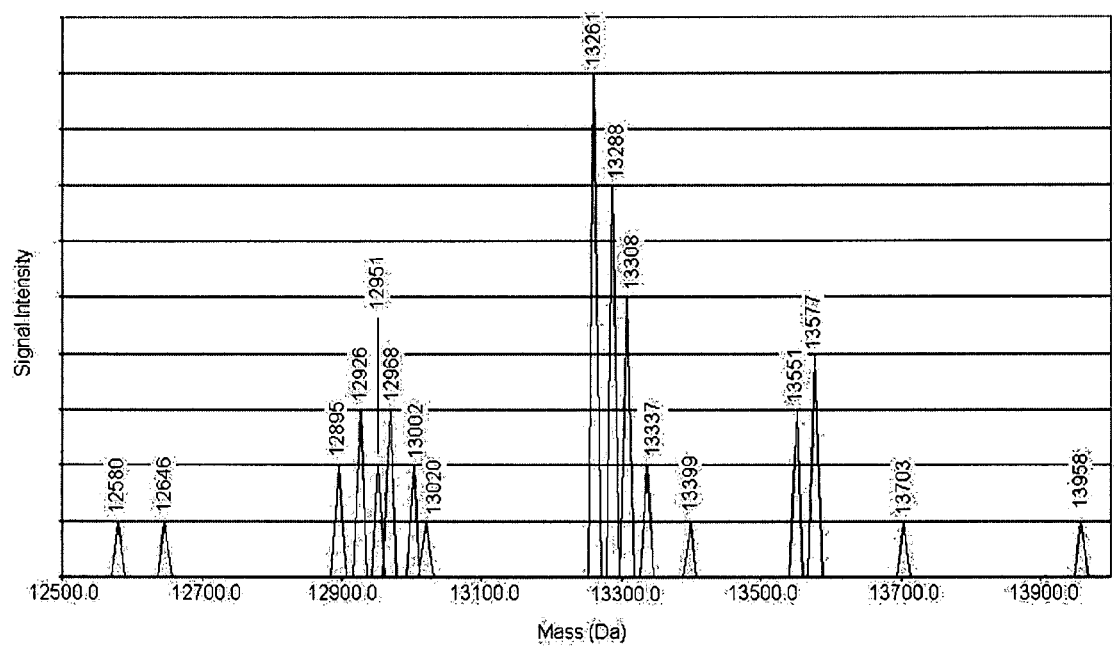
FIG. 1 is a theoretical trace generated from the data in Table 1 of Example 1 using Microsoft Excel®.

The proposed method involves generating a theoretical ESI trace (Fingerprint) and then comparing the actual ESI data of the mix to the fingerprint as a QC check. The method enables multiple data points from the ESI data to be graphically represented even if more than one oligonucleotide sequence in the assay shares the same data point. The theoretical trace assigns a signal value of one to each discrete mass, i.e. a molecular weight range that has no overlap with another range would be assigned a value of one. If more than one mass appears at the respective molecular weight, the intensity increases by that number (e.g. if three different oligonucleotides in the assay would have the same molecular weight, then the range would be assigned an intensity value of 3). The number of peaks would be further pared back by assuming that any that crossed at 50% or more of the peak height would be additive. The width of the peak is dependent on the length of the sample oligonucleotide. The new peak's mass would be calculated using the following Formula 1:

$$MW_{new} = (MW_1 * Intensity_1 + MW_2 * Intensity_2 + \ldots MW_n * Intensity_n)/(Intensity_1 + Intensity_2 + \ldots Intensity_n)$$

The new peak intensity is simply the addition of the individual intensities.

A sample containing each of the oligonucleotides of interest is prepared (a "multi-oligonucleotide sample"), and the resulting sample is run through the ESI instrument. Peaks representing the oligonucleotides in the sample would be present, and there would be higher peaks at points where multiple oligonucleotides have the same or nearly the same molecular weights. In one embodiment, a standard fingerprint could represent a standard assay kit wherein the oligonucleotide set is always the same.

In another embodiment, the invention can be incorporated into a processor to provide for an automated verification of the oligonucleotide mixture. The algorithm in Formula 1 can be a component of software that would process the given molecular weights of the individual oligonucleotide constituents that are expected to comprise an oligonucleotide mixture into the calculated peak or set of peaks. In another embodiment, the processor can work with an instrument that provides a measured mass spectrum to provide an automated system to determine whether the measured mass spectrum aligns with the calculated spectrum.

The term "multiple oligonucleotides" refers to more than one oligonucleotide sample, wherein the samples may or may not have the same molecular weight, and the samples may or may not have the same sequence. For example, Example 1 contains 48 oligonucleotide samples, i.e. a multiple oligonucleotide sample with 48 oligonucleotides.

The terms "mass spectrometry", "mass spectrum" and "mass assessment" encompass a number of technologies for both ionization methods and mass analysis. Examples of mass spectrometry formats include MALDI-TOF (Matrix Assisted Laser Desorption Ionization Time of Flight); ESI-TOF (Electrospray Ionization Time of Flight); ESI (Electrospray Ionization generally with a single or triple quadrupole(s)); ESI-QIT (Electrospray Ionization Quadrupole Ion Trap (Linear or 3-D)); MALDI-QIT (Matrix Assisted Laser Desorption Ionization Quadrupole Ion Trap (Linear or 3-D)); MADLI-QTOF (Matrix Assisted Laser Desorption Ionization Quadrupole Time of Flight); and ESI-QTOF (Electrospray Ionization Quadrupole Time of Flight).

There are conventionally two ways to ionize oligonucleotides (MALDI and ESI). Although MALDI is typically connected to TOF (Time of Flight) mass analyzers, they can be connected to Quadrupole Ion Trap (QIT) mass analyzers. ESI systems can be connected to TOF mass analyzers, as well as with Quadrupoles (both single Q and triple Q) or Quadrupole Ion Traps (both Linear and 3-D). There are also hybrid systems such as QTOF, which analyze ions from either a MALDI or ESI source first by a Quadrupole and then by TOF. To any TOF one can add rTOF (reflectron Time of Flight) or one could add an FT (Fourier-Transform) to a number of the aforementioned detectors.

The following example further illustrates the invention but, of course, should not be construed as in any way limiting its scope.

EXAMPLE 1

This example demonstrates the accuracy of the theoretical fingerprint method using a 48-oligonucleotide sample. The expected molecular weight of each oligonucleotide was calculated and entered into Table 1. As shown in Table 1, 19 oligonucleotides have the same molecular weight. The peaks were calculated to be 20 Da wide to coincide with the general width of the sample oligonucleotides, and overlapping peaks were combined.

TABLE 1

| Actual Molecular Weight of Oligonucleotide Set | |
|---|---|
| Oligonucleotide | Actual MW |
| 1 | 12580.2 |
| 2 | 12646.2 |
| 3 | 12895.4 |
| 4 | 12895.4 |
| 5 | 12919.4 |
| 6 | 12924.4 |
| 7 | 12933.4 |
| 8 | 12947.4 |
| 9 | 12955.4 |
| 10 | 12964.4 |
| 11 | 12970.4 |
| 12 | 12970.4 |
| 13 | 12997.5 |
| 14 | 13006.5 |
| 15 | 13020.4 |
| 16 | 13253.6 |
| 17 | 13254.6 |
| 18 | 13259.6 |
| 19 | 13260.6 |
| 20 | 13262.6 |
| 21 | 13262.6 |
| 22 | 13263.6 |
| 23 | 13263.6 |
| 24 | 13268.6 |
| 25 | 13276.6 |
| 26 | 13286.6 |
| 27 | 13286.6 |
| 28 | 13286.6 |
| 29 | 13290.6 |
| 30 | 13290.6 |
| 31 | 13295.6 |
| 32 | 13302.6 |
| 33 | 13306.6 |
| 34 | 13308.6 |
| 35 | 13311.7 |
| 36 | 13311.7 |

TABLE 1-continued

Actual Molecular Weight of Oligonucleotide Set

| Oligonucleotide | Actual MW |
|---|---|
| 37 | 13334.6 |
| 38 | 13339.7 |
| 39 | 13398.7 |
| 40 | 13548.8 |
| 41 | 13551.8 |
| 42 | 13551.8 |
| 43 | 13573.8 |
| 44 | 13573.8 |
| 45 | 13575.8 |
| 46 | 13584.8 |
| 47 | 13703.9 |
| 48 | 13958.0 |

Using Formula 1, the oligonucleotides were plotted in a graph based upon their molecular weight. FIG. 1 shows a chart of the data from Table 1 using Formula 1 using Microsoft® Excel®.

The first step in designing the theoretical trace was to first combine the oligonucleotide samples that had the same molecular weights by assigning intensities equal to the number of samples that had the same molecular weight. Then Formula 1 was applied to all peak sets until the overlap was less than 50% between all peaks To illustrate how the peaks were further combined to result in the FIG. 1 trace, a subset (outlined in FIG. 5) of the data was chosen to explain the next step.

Figure 5:
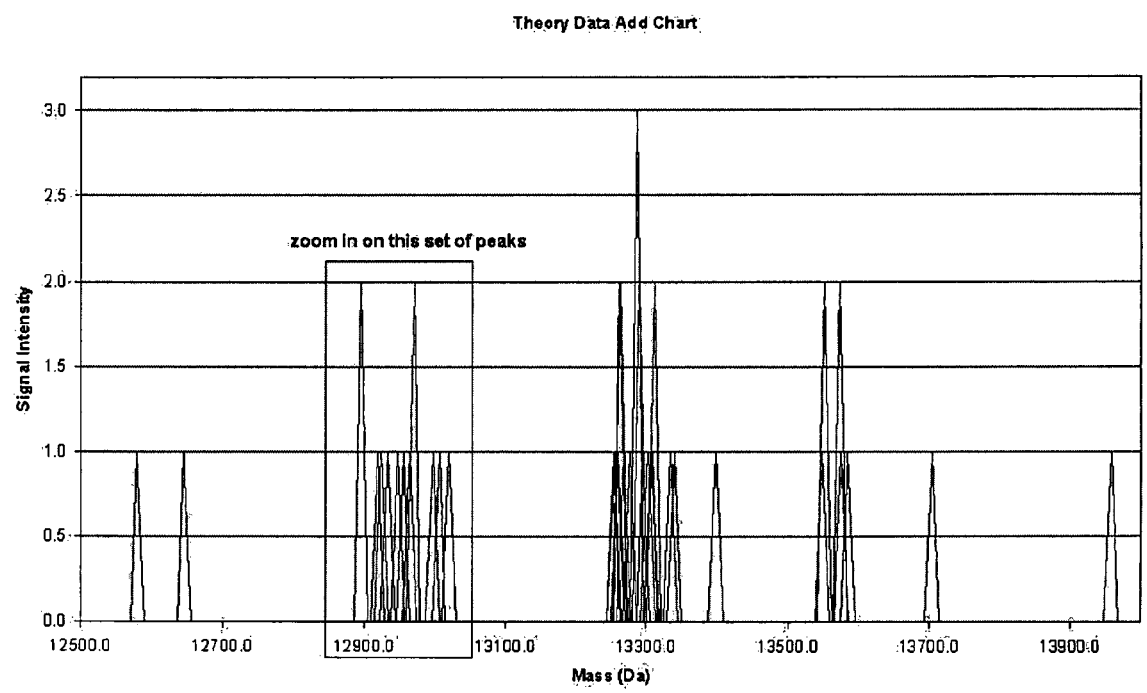
FIG. 5 is a graph of the data in Table 1 wherein the intensity is equal to the amount of oligonucleotide samples with the same molecular weight.
Figure 6:
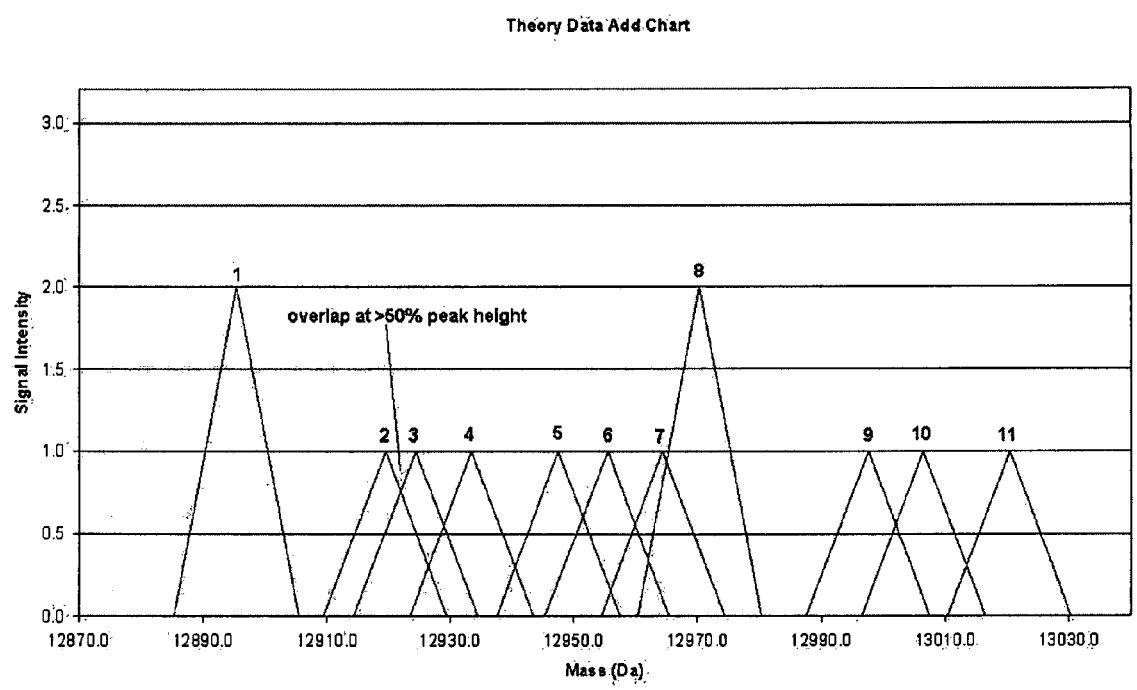
FIG. 6 is a magnified version of the data outlined in FIG. 5.
Figure 7:
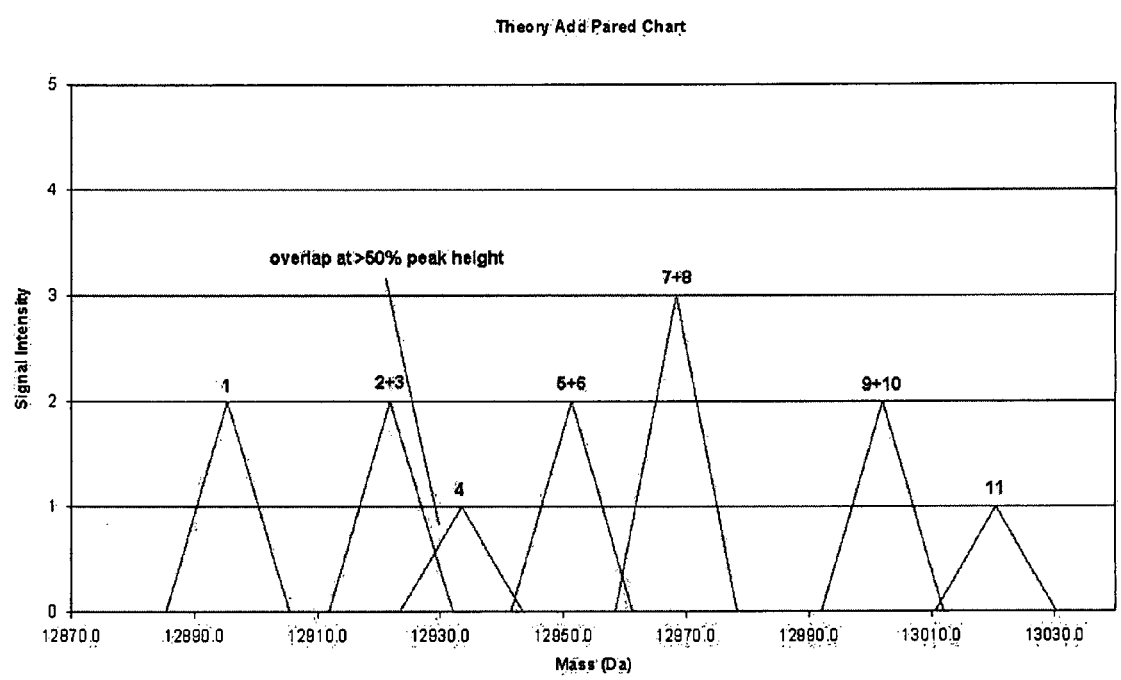
FIG. 7 depicts the amount of overlap between peaks (2+3) and 4 to illustrate why peak 4 is combined with peaks 2 and 3 to form one peak in the theoretical trace in FIG. 1.

FIG. 6 is a magnified version of the data outlined in FIG. 5. Peaks 1 and 11 did not overlap any other peaks and therefore they remained independent peaks. The peaks where there was overlap at greater than 50% peak height were combined using Formula 1. For example peaks 2, 3 and 4 would be combined because they all overlap at greater than 50% peak height. In particular, peaks 2 and 3 were added using Formula 1 ((12914.4*1+12924.4*1)/(1+1)=12921.9, Intensity=2), and the resulting sum was added to peak 4, ((12921.9*2+12933.4*1)/(2+1)=12925.7, Intensity=3) because the peak resulting from the sum of (2+3) overlapped peak 4 at greater than 50% of the peak height of peak 4. See FIG. 7 for an illustration of (2+3) peak against peak 4.

Figure 8:
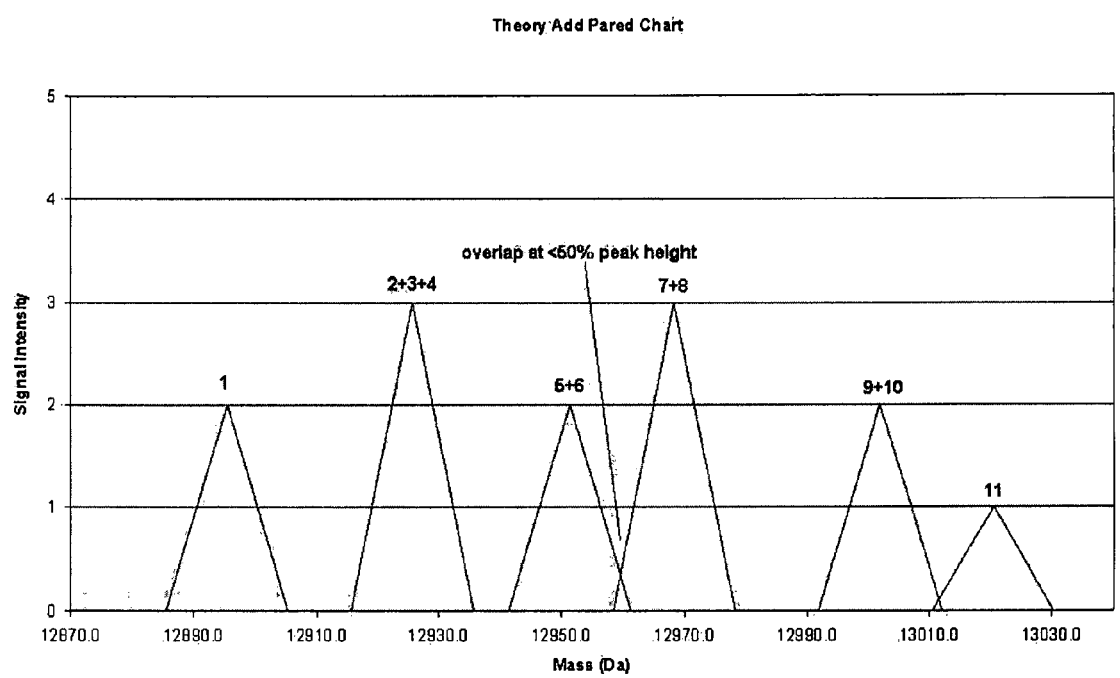
FIG. 8 illustrates the gap (no overlap at greater than 50% peak height) between peaks (5+6) and (7+8) that would require separating the two peaks for the theoretical trace.

Peaks 5 and 6 were combined to form 1 peak, and peaks 7 and 8 were combined to form another peak. Although peaks 6 and 7 overlap at greater than 50% peak height, the respective sets of peaks (5+6) and (7+8) had a greater overlap than 6 and 7 do to each other. Once the greater overlap peaks were calculated ((5+6) and (7+8)), there was no overlap greater than 50% between (5+6) and (7+8) and therefore were not combined. See FIG. 8.

Figure 2:
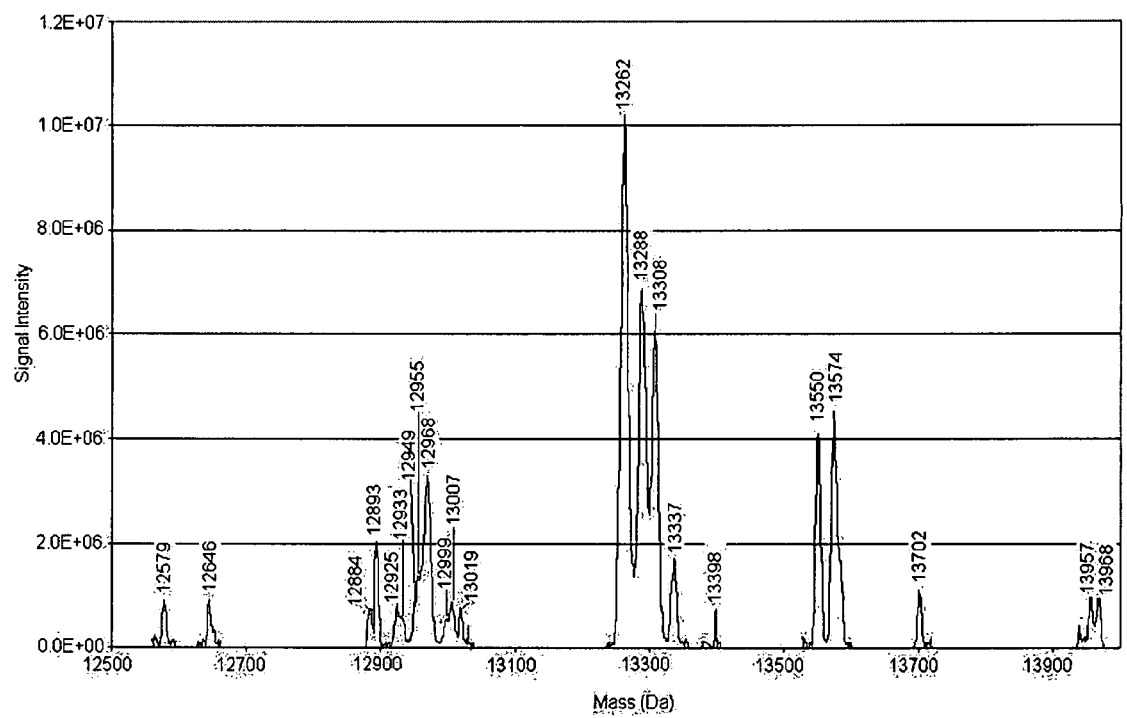
FIG. 2 is an actual ESI trace of the 48 samples in Example 1.
Figure 3:
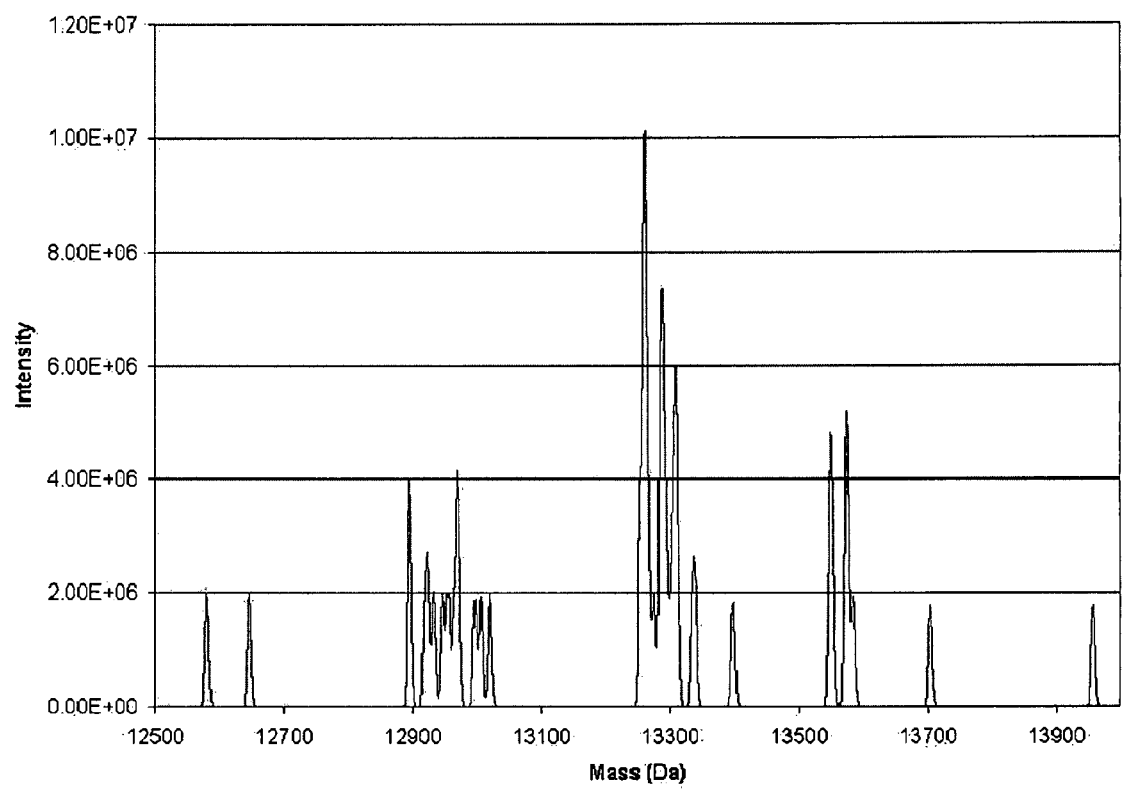
FIG. 3 is a theoretical trace generated from the data in Table 1 of Example 1 using Data Explorer™ software from Applied Biosystems.
Figure 4:
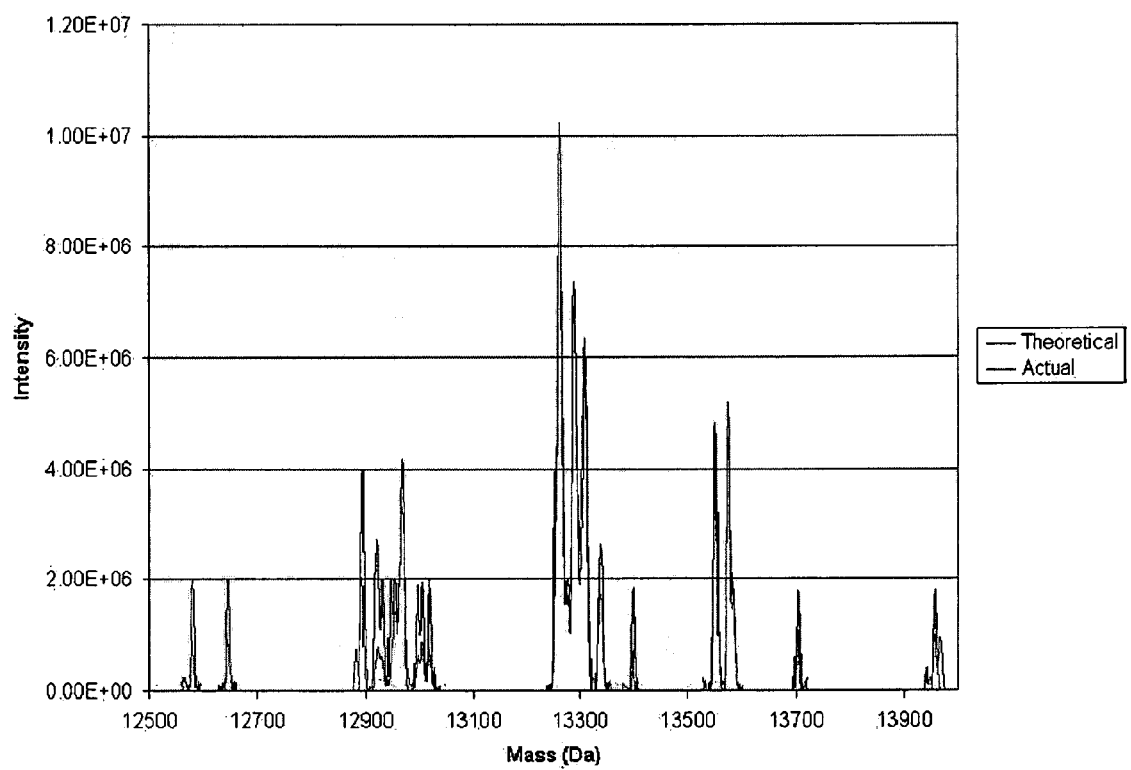
FIG. 4 is an overlay of the theoretical trace in FIG. 3 and the actual ESI data from FIG. 2.

Another theoretical chart was generated using Formula 1 with the data from Table 1 with DataExplorer™ software from Applied Biosystems (FIG. 3). A sample containing all 48 oligonucleotides was loaded into an LCQ™ ESI instrument from Thermo Fisher Scientific to generate the actual trace. FIG. 2 contains the actual ESI trace data. FIGS. 2 and 3 were overlaid (FIG. 4) to demonstrate the correlation between the expected and actual peak values. The results demonstrate that each peak in the actual trace has a corresponding peak in the theoretical traces, and the actual trace contains each peak that was present in the theoretical fingerprints.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of detecting the presence or absence of a constituent oligonucleotide in an oligonucleotide mixture, the method comprising:

a) obtaining a measurement of a mass spectrum of the oligonucleotide mixture;

b) comparing the measurement of the mass spectrum having a plurality of measured peaks with a calculated mass spectrum having a plurality of calculated peaks, said calculated mass spectrum derived from Formula 1:

$$MW_{new} = (MW_1 * Intensity_1 + MW_2 * Intensity_2 + \ldots MW_n * Intensity_n) / (Intensity_1 + Intensity_2 + \ldots Intensity_n)$$

wherein $MW_{new}$ is a calculated molecular weight of a calculated peak, $MW_1$ is a first molecular weight of a first subset of one or more oligonucleotides in the oligonucleotide mixture, $MW_2$ is a second molecular weight of a second subset of one or more oligonucleotides in the oligonucleotide mixture, $MW_n$ represents one or more additional molecular weights of one or more additional n subsets in the oligonucleotide mixture, $Intensity_1$ is a first peak intensity of the first subset of one or more oligonucleotides in the oligonucleotide mixture, $Intensity_2$ is a second peak intensity of the second subset of one or more oligonucleotides in the oligonucleotide mixture and $Intensity_n$ represents one or more additional peak intensities of the one or more additional n subsets in the oligonucleotide mixture; and c) detecting the presence or absence of the constituent oligonucleotide by correlating one or more of the measured peaks with one or more of the calculated peaks.

2. The method according to claim 1 wherein the mass spectrum is a mass spectrometry trace.

3. The method according to claim 1 wherein the mass spectrum is an electrospray ionization mass spectroscopy trace.

4. The method according to claim 1 wherein the mass spectrum is a matrix assisted laser desorption ionization time-of-flight mass spectrometry.

5. The method according to claim 1 wherein the mass spectrum is an Electrospray Ionization Quadrupole Ion Trap.

6. The method according to claim 1 wherein the mass spectrum is a Matrix Assisted Laser Desorption Ionization Quadrupole Ion Trap.

7. The method according to claim 1 wherein the mass spectrum is a Matrix Assisted Laser Desorption Ionization Quadrupole Time of Flight.

8. The method according to claim 1 wherein the mass spectrum is an Electrospray Ionization Quadrupole Time of Flight.

9. The method of claim 1 wherein the calculated mass spectrum is provided by a processor, wherein said processor accepts a set of given molecular weights of the oligonucleotide mixture to provide a calculated mass spectrum.

10. A kit for an assay utilizing a standard set of oligonucleotides, said kit comprising the standard set of oligonucleotides and a mass spectrum calculated as in claim 1.

11. A method for predicting a measured peak intensity and a measured peak mass in an electrospray ionization mass spectroscopy trace, the method comprising:
  a) assigning each oligonucleotide member in a sample an initial intensity value of one;
  b) determining from a set of oligonucleotide members a first sub-set of oligonucleotide members that have an equal molecular weight;
  c) combining members of the first sub-set to form a combined first peak intensity using a formula:

$$I_{new}=I_1+I_2+\ldots I_n$$

wherein $I_{new}$ is the first combined peak intensity and $I_1$ and $I_2$ are intensities of the oligonucleotide members of the first sub-set and $I_n$ represents additional oligonucleotide members that may or may not be present in the first sub-set that have an equal molecular weight as $I_1$ and $I_2$;
  d) assigning a first combined peak mass to the first combined peak intensity that correlates with the molecular weight of each member of the first sub-set;
  e) determining from the set of oligonucleotide members a second sub-set of oligonucleotide members, said second sub-set of oligonucleotide members having a molecular weight within a range of other members of the second sub-set that when each member of the second sub-set is plotted as a peak in an electrospray ionization mass spectroscopy trace the peaks of members of the second sub-set overlap at greater than 50 percent peak height;
  f) combining members of the second sub-set to form a second combined peak intensity using a formula:

$$I2_{new}=I2_1+I2_2+\ldots I2_n$$

wherein $I2_{new}$ is the second combined peak intensity and $I2_1$ and $I2_2$ are intensities of the oligonucleotide members of the second sub-set and $I2_n$ represents additional oligonucleotide members that may or may not be present in the second sub-set;
  g) combining the members of the second sub-set to form a second combined peak mass using the formula:

$$MW_{new}=(MW_1*I2_1+MW_2*I2_2+\ldots MW_n*I2_n)/(I2_1+I2_2+\ldots I2_n)$$

wherein $MW_{new}$ represents the second combined peak mass, $MW_1$ and $MW_2$ are the molecular weights of members of the second sub-set, and $MW_n$ represents additional n members that may be present in the second sub-set; and predicting a measured peak intensity and a measured peak mass in an electrospray ionization mass spectrometry trace from the second combined peak intensity and the second combined peak mass.

* * * * *